United States Patent [19]

Matsumoto et al.

[11] Patent Number: 5,097,037

[45] Date of Patent: Mar. 17, 1992

[54] PROCESS FOR THE OPTICAL RESOLUTION OF PYRANOBENZOXADIAZOLE COMPOUNDS

[75] Inventors: Hiroo Matsumoto; Kiyotomo Seto; Ryozo Sakoda, all of Funabashi, Japan

[73] Assignee: Nissan Chemical Industries, Ltd., Tokyo, Japan

[21] Appl. No.: 551,795

[22] Filed: Jul. 12, 1990

[30] Foreign Application Priority Data

Jul. 17, 1989 [JP] Japan .................................. 1-183970
May 24, 1990 [JP] Japan .................................. 2-134724

[51] Int. Cl.⁵ ............................................ C07D 498/04
[52] U.S. Cl. ..................................................... 548/126
[58] Field of Search ........................... 514/364; 548/126

[56] References Cited

U.S. PATENT DOCUMENTS 4,900,752 2/1990 Seto ..................................... 514/364

OTHER PUBLICATIONS

Ashwood, J. Med. Chem. 29 2194 (1986).

Primary Examiner—Robert Gerstl
Attorney, Agent, or Firm—Oliff & Berridge

[57] ABSTRACT

A process for the optical resolution of a pyranobenzoxadiazole compound represented by the formula [(±)I]:

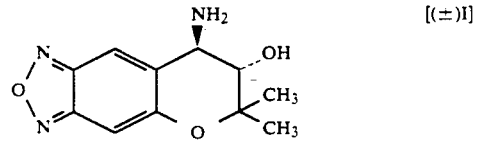

which comprises reacting the compound [(±)I] with an optically active carboxylic acid represented by the formula [II]:

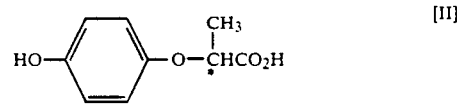

and separating the diastereomeric salt thus formed is disclosed.

1 Claim, No Drawings

PROCESS FOR THE OPTICAL RESOLUTION OF PYRANOBENZOXADIAZOLE COMPOUNDS

BACKGROUND OF THE INVENTION

1. Field of the Invention

This invention relates to an optically active pyranobenzoxadiazole compound, which is an important intermediate in the synthesis of an optically active pyranobenzoxadiazole derivative useful for the treatment of hypertension and asthma, and a process for the optical resolution of a pyranobenzoxadiazole compound.

2. Description of the Prior Art

A pyranobenzoxadiazole derivative represented by the formula [III] (which will be briefly referred to as the compound [III] hereinafter):

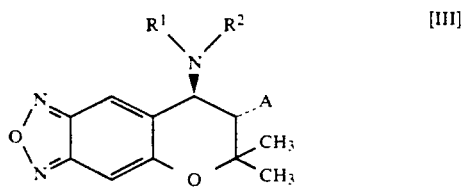

wherien A represents a hydroxyl group or an OC-(O)$CH_{3-n}X_n$ group which X represents a fluorine atom, a chlorine atom, a bromine atom, a methyl group or a methoxy group and n represents 0 or an integer of 1 to 3;

when $R^1$ represents a hydrogen atom, $R^2$ represents a hydrogen atom, C(Z)$CH_{3-n}X_n$ group, in which Z represents an oxygen atom or a sulfur atom and X and n is as defined above, or C(Z)NH$CH_{3-n}X_n$ group, in which Z and n are defined above; and when $R^1$ does not represent a hydrogen atom, $R^1$ and $R^2$ together represent $(CH_2)_{m-1}C(Z)$ group, in which m represent an integer of 4 or 5 and Z is as defined above, $(CH_2)_{m-2}NHC(Z)$ group or a $(CH_2)_{m-2}OC(Z)$ group, in which Z and m are as defined above, is obtained in the form of a racemic mixture as described in Japanese Patent Laid-Open No. Hei 2-49788 (49788/1990) and U.S. Pat. No. 4,900,752. The compound [III] exerts intense vasodilatory and hypotensive activities and thus is expected to be useful as a medicine for treating hypertension, angina pectoris, arrhythmia, cerebral circulation disorders and asthma.

As described in the Japanese Patent Laid-Open No. Hei 2-49788 (49788/1990), the compound [III] can be synthesized in the following manner:

Reaction Scheme 1

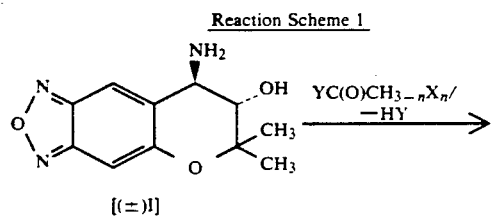

-continued
Reaction Scheme 1

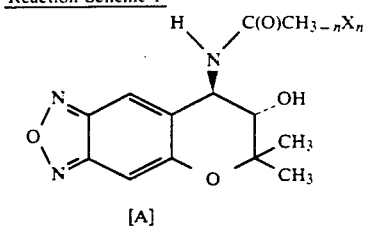

[A]

Reaction Scheme 2

Compound [(±)I] $\xrightarrow[\text{(catalyst)}]{C(O)NCH_{3-n}X_n \text{ or } X_nCH_{3-n}NC(S)}$

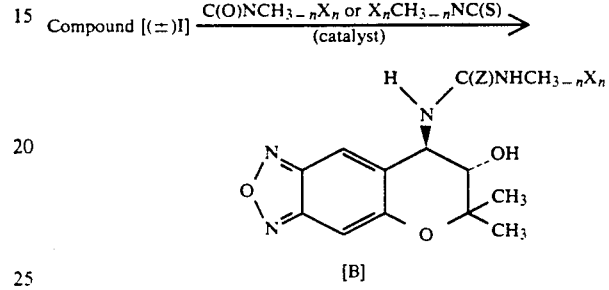

[B]

Reaction Scheme 3

Compound [(±)I] $\xrightarrow[-HY^1]{(1) YC(O)(CH_2)_{m-1}Y^1/} \xrightarrow{(2) -HY^1}$

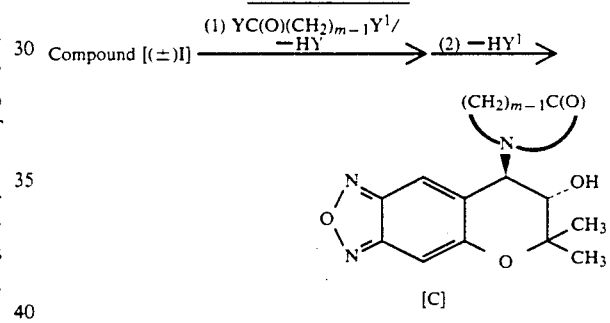

[C]

Reaction Scheme 4

Compound [(±)I] $\xrightarrow[Y^1(CH_2)_{m-2}NC(S)]{(1) (O)CN(CH_2)_{m-2}Y^1/ \text{(catalyst)}} \xrightarrow{(2) -HY^1}$

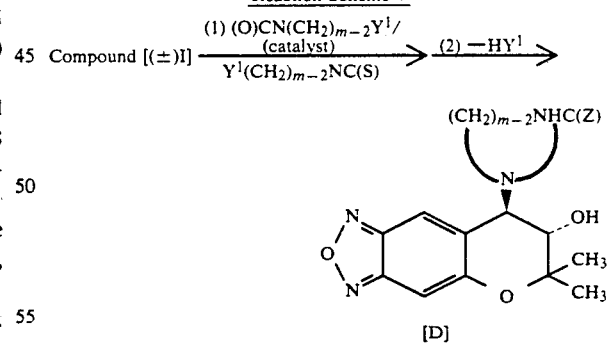

[D]

Reaction Scheme 5

Compound [(±)I] $\xrightarrow{(1)YC(O)O(CH_2)_{m-2}Y^1/-HY (2)-HY^1}$ [E]

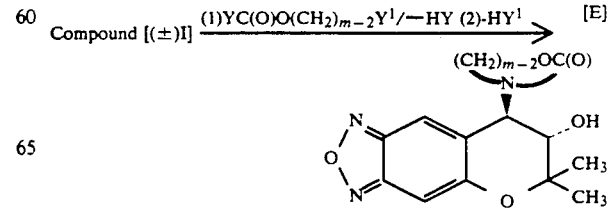

In above reaction schemes, Y represents an leaving group such as a halogen atom (for example, a chlorine, bromine or iodine atom), an acetoxy group or a trifluoroacetoxy group;

Y¹ represents a chlorine atom, a bromine atom, an iodine atom, an o- or p-toluenesulfonate group or a methanesulfonate group; and m, n and X are as defined above.

The compound [A], which is a compound [III] wherein R¹ represents a hydrogen atom, can be prepared by reacting a pyranobenzoxadiazole compound, which is obtained in the form of a racemic mixture (briefly referred to as the compound [(+)I] hereinafter), with an acylating agent $YC(O)CH_{3-n}X_n$, in which X, Y and n are as defined above, optionally in the presence of a base (refer to Reaction Scheme 1).

The compound [C], which is a compound [III] wherein R¹ represents a hydrogen atom, can be prepared by reacting the compound [(±)I] with an isocyanate $C(O)NCH_{3-n}X_n$ or isothiocyanate $X_nCH_{3-n}NC(S)$ in which X, Z and n are as defined above (refer to Reaction Scheme 2).

The compound [C], which is a compound [III wherein R¹ and R² together represent $(CH_2)_{m-1}C(O)$ group, can be prepared by reacting the compound [(±)I] with an acylating agent $YC(O)(CH_2)_{m-1}Y^1$, in which Y, Y¹ and m are as defined above, optionally in the presence of a base and then cyclizing the reaction product optionally in the presence of a base (refer to Reaction Scheme 3).

The compound [D], which is a compound [III] wherein R¹ and R² together represent $(CH_2)_{m-2}NHC(Z)$ group in which Z and m are as defined above, can be prepared by reacting the compound [(±)I] with an isocyanate $(O)CN(CH_2)_{m-2}Y^1$ or isothiocyanate $(S)CN(CH_2)_{m-2}Y^1$, in which Y¹ and m are as defined above, and then cyclizing the reaction product optionally in the presence of a base (refer to Reaction Scheme 4).

The compound [E], which is a compound [III] wherein R¹ and R² together represent $(CH_2)_{m-2}OC(O)$ group in which m is as defined above, can be prepared by reacting the compound [(±)I] with a halogenocarbonate $YC(O)O(CH_2)_{m-2}Y$, in which Y, Y¹ and m are as defined above, optionally in the presence of a base and then cyclizing the reaction product optionally in the presence of a base (refer to Reaction Scheme 5).

In the above reaction schemes, a compound if [III] wherein Z is a sulfur atom may be obtained by sulfurizing the corresponding compound wherein Z is an oxygen atom with Lawesson's reagent.

As described in the Japanese Patent Laid-Open No. Hei 2-49788 (49788/1990), the compound [(±)I] may be prepared in the following manner:

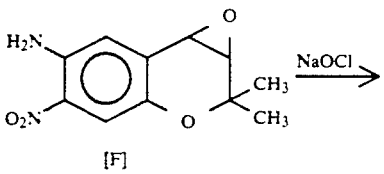
[F]

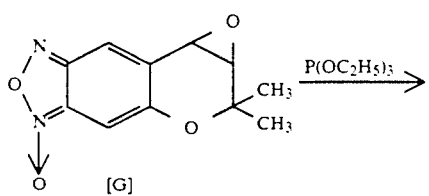
[G]

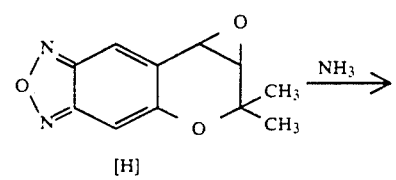
[H]

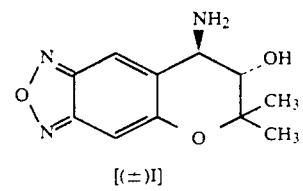
[(±)I]

The compound [(±)I] may be obtained by treating a known compound [F] with sodium hypochlorite, reducing N-oxide group of the compound [G] thus formed with a reducing agent such as triethyl phosphite and then reacting the compound [H] thus formed with ammonia in an inert solvent.

However, there has never been reported the optical resolution of the compound [(±)I].

Furthermore, the above-mentioned racemic compound [III], which carries asymmetric carbon atoms at the 3- and 4-positions of the pyran ring, has two optical isomers (compound [III*] and [III**]). However, the above Japanese Patent Laid-Open No. Hei 2-49788 (49788/1990) describes neither these optically active pyranobenzoxadiazole derivatives nor any process for the production of the same.

In the field of medicines, it is frequently observed that optical isomers are different from each other in pharmacological activity and safety. Therefore, it is desirable to optically resolve these isomers in order to develop better medicines.

The present inventors have found out that an optically active pyranobenzoxadiazole derivative (corresponding to the compound [III*]), which is synthesized via an optically active pyranobenzoxadiazole compound showing dextrorotation in ethanol (corresponding to the compound [(±)I] which will be described hereinafter), is remarkably superior to an optically active pyranobenzoxadiazole derivative (corresponding to the compound [III**]), which is synthesized via an enantiomer (corresponding to the compound [(−)I] which will be described hereinafter), from the viewpoint of medicinal activities, thus completing the present invention.

SUMMARY OF THE INVENTION

Accordingly, the present invention relates to a process for the optical resolution of the compound [(±)I] which comprises reacting the pyranobenzoxadiazole compound of the formula [(±)I]:

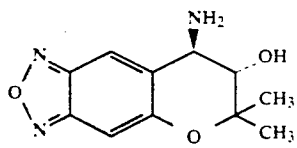

in the form of a racemic mixture with an optically active carboxylic acid of the formula [II]:

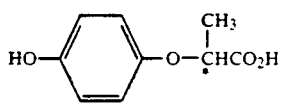

which will be briefly referred to as the compound [II] hereinafter, and then separating the diastereomeric salt thus formed. Further, the present invention relates to an optically active pyranobenzoxadiazole compound [(±)I showing dextrorotation in ethanol (corresponding to the above compound [(+)I] between the two optical isomers obtained by the above-mentioned process.

The compound [II], which is an optically resolving agent and occurs as two optical isomers of the compound [(+)II] and [(−)II], may be synthesized by a method described in Japanese Patent Laid-Open No. Sho 61-83144 (83144/1986).

Now, the process for optically resolving the compound [(±)I] into the compound [(±)I], and the enantiomer thereof, namely [(−)I] will be described in detail.

[Reaction Scheme I]

Step A

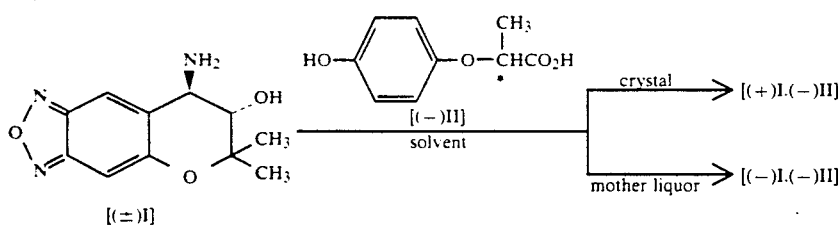

Step B

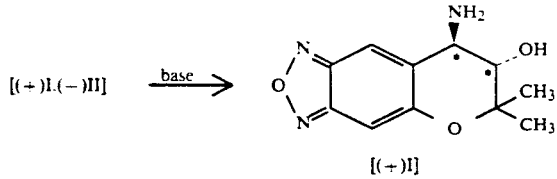

In the step A, the compound [(±)I] is reacted with the compund [(−)II], which is used as an optically resolving agent, and crystallized. Thus a diastereomeric salt [(±)I·(−)II] can be easily obtained in the form of crystals.

It is to be noted here, however, the obtained crystals may be solvated depending on the solvent used (refer to Examples).

Likewise, a diastereomeric salt [(−)I·(±)II] can be easily obtained by using the compound [(+)II] as an optically resolving agent.

Thus the desired optical isomer of the compound [(+)I] can be easily obtained by appropriately selecting the resolving agent.

As the solvent to be used in the step A, ketones such as acetone and methyl isobutyl ketone are preferable, though the present invention is not restricted thereby. In this case, the diastereomeric salt is crystallized out in the form of a solvate.

The reaction temperature may usually range from −20° to 100° C., preferably from 10° to 30° C.

The crystallization temperature may usually range from −20° to 50° C., preferably from −10° to 20° C.

The diastereomeric salt thus crystallized out may be further recrystallized from, for example, acetone to thereby give a crystalline diastereomeric salt of a high purity.

In the step B, the crystalline diastereomeric salt [(+)I·(−)II] or a solvate thereof is reacted with a base selected from among sodium hydrogencarbonate, potassium hydrogencarbonate, sodium carbonate, potassium carbonate, sodium hydroxide and potassium hydroxide. Thus the target compound [(+)I] showing dextrorotation in ethanol can be easily obtained.

Likewise, the compound [(−)I] can be easily obtained from the diastereomeric salt [(−)I·(+)II] or a solvate thereof.

The optical purity of the compound [(+)I] can be determined by reacting said compound with methyl isocyanate to thereby give a urea compound of the formula [(+)IV].

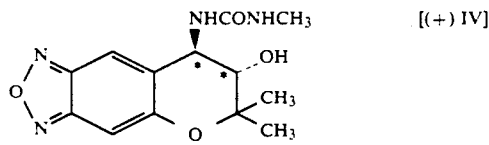

and then analyzing the obtained compound with the use of an optically active liquid chromatographic column (Chiralcel OC mfd. by Daicel Chemical Industries, Ltd.).

The optical purity of the compound [(−)I] can be determined in the same manner.

As will be shown hereinafter in Test Example, the compound [III*] prepared from the compound [(+)I] in accordance with the method described in the above-mentioned Japanese Patent Laid-Open No. Hei 2-49788 (49788/1990) shows an extremely high activity of lowering blood pressure, as compared with the enantiomer (compound [III**]) prepared from the compound [[(−)I]].

It is obvious, therefore, that the application of the compound [III*] to the treatment of, for example, hypertension is more effective than the application of the compound [III].

An analysis with the use of an optically active liquid chromatographic column (Chiralcel OC, mfd. by Daicel Chemical Industries, Ltd.) has proved that no racemization occurs during the preparation of the compound [III*] from the compound [(+)I] or the preparation of the compound [III**] from the compound [(−)I].

methylcellulose and forcedly administered to three male spontaneously hypertensive rats aged 11 weeks via an oral route with the use of a gastric probe.

The animals were prewarmed in a warm box at 50° C. for three to five minutes and then transported into a restraining cage at 37° C. to measure the systolic blood pressure by a tail-cuff method (KN-210-1, mfd. by Natsume Seisakusho Co., Ltd.). Table 1 gives the percentage lowering of blood pressure one hour after the administration. Each value represents the mean of the three animals.

Table 2 gives the analytical data of the compounds [III*] and [III**].

TABLE 1

| $R^1 \diagdown N \diagup R^2$ | Compound [III*] (enantiomer from compound [(+)I]) | | Compound [III**] (enantiomer from compound [(−)I]) | |
|---|---|---|---|---|
| | Dose (mg/kg) | Lowering of blood pressure (%) | Dose (mg/kg) | Lowering of blood pressure (%) |
| (piperidinone) | 0.1 | 37 | 3.0 | 9 |
| CH₃CH₂CONH | 0.3 | 23 | 3.0 | 1 |
| CH₃NHCONH | 0.3 | 17 | 3.0 | 4 |

TEST EXAMPLE, EXAMPLES AND REFERENTIAL EXAMPLES (1) Test Example (hypotensive activity)

The compounds [III*] and [III**] were each dissolved or suspended in a 0.5% aqueous solution of

TABLE 2

| $R^1 \diagdown N \diagup R^2$ | Compound [III*] (enantiomer from compound [(+)I]) | | Compound [III**] (enantiomer from compound [(−)I]) | |
|---|---|---|---|---|
| | m.p. (°C.) | Retention time in optically active liquid chromatography (min) | m.p. (°C.) | Retention time in optically active liquid chromatography (min) |
| (piperidinone) | 180–182 | 15.4 | 180–182 | 14.3 |
| CH₃CH₂CONH | 179–180 | 9.7 | 179–180 | 9.0 |
| CH₃NHCONH | 165–167 | 13.8 | 165–167 | 12.0 |

Optically active liquid chromatography
column: Chiralcel OC (Daicel Chemical Industries, Ltd.)
eluent: hexane/ethanol (4:1 v/v)
column temperature: 40° C.
flow rate: 0.5 ml/min
detection: UV absorption (254 nm)
Every sample used in the hypotensive activity test has an optical purity of 100% e.e., determined by the above-mentioned optically active liquid chromatography.

(2) Examples

Example 1

(a) Step A: resolution of diastereomeric salt [(+)I·(−)II acetone solvate] and diastereomeric salt [(−)I·(+)II acetone solvate]

117.6 g (0.500 mol) of (±)-7,8-dihydro-6,6-dimethyl-7-hydroxy-8-amino-6H-pyrano[2,3-f]benz-2,1-3-oxadiazole (compound [(±)I]) and 92.9 g (0.510 mol) of (−)-2-(4hydroxyphenoxy)propionic acid (compound [(−)II]) were dissolved in 1000 g of acetone and stirred for three hours under ice-cooling.

The crystals thus precipitated were filtered by means of suction, washed with 500 ml of ice-cooled acetone and dried under reduced pressure. Thus 64.6 g of a diastereomeric salt [(±)I·(−)II acetone solvate] was obtained in the form of pale yellow crystals (yield: 27.2%, optical purity: 95.7% e.e.).

This diastereomeric salt [(+)I·(−)II acetone solvate] was heated under reflux in 270 g of acetone and then 77 g of the acetone was distilled off. The residue was crystallized out under ice-cooling for two hours. Thus the optical purity of the diastereomeric salt [(+)I·(−)II acetone solvate] was elevated to 100% e.e. (yield: 80%).

In the measurement of the m.p. of this product, it began to slowly decompose from around 102° C. As a result of nonaqueous titration with perchloric acid in acetic acid, it was confirmed that one molecule of acetone was solvated.

On the other hand, the filtrates were combined and the acetone was distilled off therefrom. Then 1500 ml of ethyl acetate, 1000 ml of water, 32.8 g (0.39 mol) of sodium hydrogencarbonate and 200 g of sodium chloride were added to the residue followed by shaking.

The obtained solution was allowed to stand to thereby cause phase separation. The ethyl acetate phase was collected and 200 ml of water, 6.56 g (0.078 mol) of sodium hydrogencarbonate and 40 g of sodium chloride were added thereto. The obtained mixture was shaken again and allowed to stand to thereby cause phase separation.

The ethyl acetate phase thus obtained was dried by adding anhydrous sodium sulfate and filtered and then the ethyl acetate was distilled off therefrom. Thus 94.7 g of a brown solid was obtained.

This brown solid and 73.4 g (0.403 mol) of (+)-2-(4-hydroxyphenoxy)propionic acid (compound -(+)II- were dissolved in 700 g of acetone and stirred under ice-cooling for three hours.

The crystals thus precipitated were filtered by means of suction, washed with 280 ml of ice-cooled acetone and then dried under reduced pressure. Thus 75.79 g of a diastereomeric salt [(−)I·(±)II acetone solvate] was obtained in the form of pale yellow crystals (yield: 31.9%, optical purity: 100% e.e.).

In the measurement of the m.p. of this product, it began to slowly decompose from around 102° C. As a result of nonaqueous titration with perchloric acid in acetic acid, it was confirmed that one molecule of acetone was solvated.

(b) Step B: resolution of compounds [(+)I] and [(−)I]

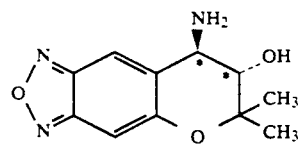

To 66.7 g (0.140 mol) of the diastereomeric salt [(+)I·(−)II acetone solvate] were added 1000 ml of ethyl acetate, 700 ml of water, 17.0 g (0.160 mol) of sodium carbonate and 140 g of sodium chloride, followed by shaking and allowing to stand to thereby cause phase separation.

The ethyl acetate phase was collected and washed with 200 ml of water, 2.1 g (0.020 mol) of sodium carbonate and 40 g of sodium chloride. Further, it was washed with an aqueous solution of sodium chloride (40 g/200 ml of water). Then the ethyl acetate phase was dried by adding anhydrous sodium sulfate and filtered. After distilling off the ethyl acetate, 31.85 g of the compound [(+)I] was obtained (yield: 96%).

Separately, the diastereomeric salt [(−)I·(+)II acetone solvate] was treated in the same manner as the one described above. Thus the compound [(−)I] was obtained.

Analytical data m.p.: 145°–146° C. (both of the compounds [(+)I] and [(−)I])

Optical rotation:
Compound [(+)I]:$[\alpha]_D^{25} +189°$ (c=0.50 EtOH)
Compound [(−)(I]:$[\alpha]_D^{25} -189°$ (c=0 50, EtOH)

Optical purity: (determined under the conditions specificed in Table 2)

Each test compound was reacted with methyl isocyanate. The urea compound thus formed was analyzed with the use of an optically active liquid chromatographic column (Chiralcel OC, mfd. by Daicel Chemical Industries, Ltd.).

The compound [(+)I] and [(−)I] showed each an optical purity of 100% e.e.

MNR spectrum:

Both of the compound [(−)I showed each a spectrum identical with that of the compound [(±)I], i.e., the racemic mixture.

NMR (CDCl$_3$+DMSO-d$_6$) (ppm): 1.26 (3H), 1.49 (3H), 2.80–3.30 (3H), 3.33 (1H), 3.78 (1H), 6.82 (1H) and 7.98 (1H)

Example 2

(a) Step A: resolution of diastereomeric salt [(+)I·(−)II methyl isobutyl ketone solvate] and diastereomeric salt [(−)I·(+)II methyl isobutyl ketone solvate]

4.70 g (20 mmol) of (±)-7,8-dihydro-6,6-dimethyl-7-hydroxy-8-amino-6H-pyrano[2,3-f]benz-2,1,3-oxadiazole (compound [(±)I]) and 3.70 g (20.3 mmol) of (−)-2-(4hydroxyphenoxy)-propionic acid (compound [(−)II]) were dissolved in 27.8 g of methyl isobutyl ketone and stirred at 21° C. for 15 minutes.

To the solution thus obtained was added 10 mg of a seed crystal [(+)I·(−)II methyl isobutyl ketone solvate]. Stirring was continued for additional two hours to thereby crystallized out the product.

Next, the stirring was ceased and the reaction mixture was allowed to stand in a refrigerator overnight.

The crystals thus precipitated were filtered by means of suction, washed with 7.1 g of cold methyl isobutyl ketone and dried under reduced pressure. Thus 4.59 g of a diastereomeric salt [(+)I·(−)II methyl isobutyl ketone solvate] was obtained in the form of pale yellow crystals (yield: 44.4%).

In the measurement of the m.p. of this product, it began to slowly decompose from around 95° C. As a result of nonaqueous titration with perchloric acid in acetic acid, it was confirmed that one molecule of methyl isobutyl ketone was solvated.

On the other hand, the filtrates were combined and 28.2 g of a 20% aqueous solution of sodium chloride and 1.22 g (11.5 mmol) of sodium carbonate were added thereto. The obtained mixture was shaken, allowed to stand to thereby cause phase separation. The methyl isobutyl ketone phase was collected and shaken again together with 9.4 g of a 20% aqueous solution of sodium chloride. Then it was allowed to stand to thereby cause phase separation.

To the methyl isobutyl ketone phase thus obtained was added 2.07 g (11.4 mmol) of (+)-2-(4-hydroxyphenoxy)-propionic acid (compound [(+)II]). After dissolving the compound by stirring at room temperature, 10 mg of a seed crystal [(−)I·(+)II methyl isobutyl ketone solvate] was added thereto to thereby crystallize out the product. Then the reaction mixture was allowed to stand in a refrigerator overnight.

The crystals thus precipitated were filtered by means of suction, washed with 7.1 g of cold methyl isobutyl ketone and dried under reduced pressure. Thus 4.25 g of a diastereomeric salt [(+)I·(−)II methyl isobutyl ketone solvate] was obtained in the form of pale yellow crystals (yield: 41.1%).

In the measurement of the m.p. of this product, it began to slowly decompose from around 95° C. As a result of nonaqueous titration with perchloric acid in acetic acid, it was confirmed that one molecule of methyl isobutyl ketone was solvated.

(b) Step B: resolution of compounds [(+)I] and [(−)I]

To 4.26 g (8.23 mmol) of the diastereomeric salt [(+)I·(−)II methyl isobutyl ketone solvate] obtained in the above step A were added 53.4 g of ethyl acetate, 42.7 g of water, 0.873 g (8.23 mmol) of sodium carbonate and 10.7 g of sodium chloride, followed by shaking and allowing to stand to thereby cause phase separation.

The ethyl acetate phase was collected and washed with 14.2 g of water and 3.6 g of sodium chloride.

The ethyl acetate phase was dried by adding anhydrous sodium sulfate thereto and filtered. After distilling off 48.6 g of the ethyl acetate, 7.3 g of hexane was added to the residue followed by crystallization under ice-cooling for three hours. Then the crystals thus precipitated were collected. Thus 1.84 g of the compound [(+)I] was obtained (yield: 95%).

The diastereomeric salt [(−)I·(+)II·methyl isobutyl ketone solvate] was treated in the same manner as the one described above. Thus the compound [(−)I] was obtained.

The compounds [(+)I] and [(−)I] showed each an optical purity of 100% e.e.

(3) Referential Examples

Referential Example 1

(a) Synthesis of (+)-7,8-dihydro-6,6-dimethyl-7-hydroxy-8-(n-(1-oxo-5-chloro)pentyl)amino-6H-pyrano[2,3 f]benz-2,1,3-oxadiazole (intermediate)

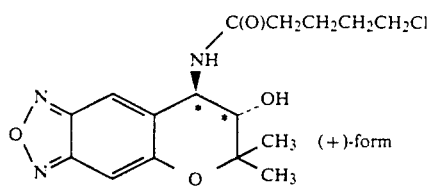

715 mg (3.04 mmol) of (+)-7,8-dihydro-6,6-dimethyl-7-hydroxy-8-amino-6H-pyrano[2,3-f]benz-2,1,3-oxadiazole [compound (+)I], 470 μl of triethylamine and 70 ml of methylene chloride were stirred at room temperature. To the obtained solution was added 430 μl (3.34 mmol) of 5-chloro-valeryl chloride. After reacting for two hours, the reaction mixture was washed with water thrice. The methylene chloride phase was dried over anhydrous sodium sulfate and filtered. After distilling off the solvent, the titled compound was obtained. This product was not purified any more but subjected to the following reaction as such.

(b) Synthesis of (+)-7,8-dihydro-6,6-dimethyl-7-hydroxy-8-(2-oxo-1-piperidinyl)-6H-pyrano[2,3-f]benz-2,1,3-oxadiazole (corresponding to compound [III*])

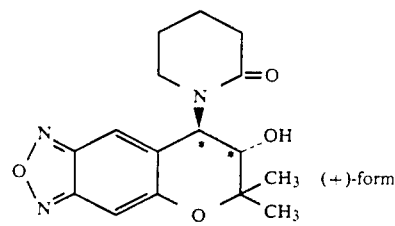

1.08 g of (+)-7,8-dihydro-6,6-dimethyl-7-hydroxy-8-(n(1-oxo-5-chloro)pentyl)amino-6H-pyrano[2,3-f]benz-2,1-3oxadiazole, 8.40 g (60.8 mmol) of potassium carbonate and 1.01 g (6.08 mmol) of potassium iodide were suspended in 200 ml of acetone and heated under reflux for nine hours in a nitrogen atmosphere.

After cooling, the insoluble matters were filtered off and the filtrate was diluted with ethyl acetate, washed with water twice and with brine once and dried over anhydrous sodium sulfate.

After distilling off the solvent, the residue was treated by preparative silica gel thin layer chromatography (developing solvent: ethyl acetate). Thus 40 mg of the titled compound was obtained (yield: 4%). Some portion of this product was then crystallized from ethyl acetate to thereby give pale yellow crystals.

Analytical data m.p.: 180°–182° C.

Optical purity: 100% e.e. (refer to Table 2)

Referential Example 2

(a) Synthesis of (−)-7,8-dihydro-6,6-dimethyl-7-hydroxy-8-(n-(1-oxo-5-chloro)pentyl)amino-6H-pyrano[2,3-f]benz-2,1,3-oxadiazole (intermediate)

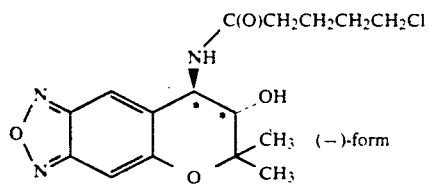

769 mg (3.27 mmol) of (−)-7,8-dihydro-6,6-dimethyl-7-hydroxy-8-amino-6H-pyrano[2,3-f]benz-2,1,3-oxadiazole [compound (−)I], 500 μl (3.60 mmol) of triethylamine and 70 ml of methylene chloride were stirred at room temperature. To the obtained solution was added 465 μl (3.60 mmol) of 5-chlorovaleryl chloride. After reacting for two hours, the reaction mixture was washed with water thrice. The methylene chloride phase was dried over anhydrous sodium sulfate and filtered. After distilling off the solvent, the titled compound was obtained. This product was not purified any more but subjected to the following reaction as such.

(b) Synthesis of (-)-7,8-dihydro-6,6-dimethyl-7-hydroxy-8-(2-oxo-1-piperidinyl)-6H-pyrano[2,3-f]benz-2,1,3-oxadiazole (corresponding to compound [III**])

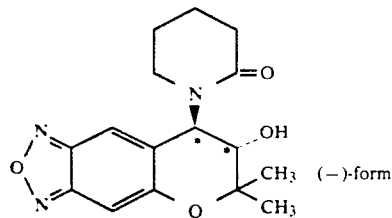

1.16 g of (−)-7,8-dihydro-6,6-dimethyl-7-hydroxy-8-(n-(1-oxo-5-chloro)pentyl)amino-6H-pyrano[2,3-f]benz-2,1,3-oxadiazole, 9.04 g (65.4 mmol) of potassium carbonate and 1.09 g (6.54 mmol) of potassium iodide were suspended in 200 ml of acetone and heated under reflux for nine hours in a nitrogen atmosphere.

After cooling, the insoluble matters were filtered off and the filtrate was diluted with ethyl acetate, washed with water twice and with brine once and dried over anhydrous sodium sulfate.

After distilling off the solvent, the residue was treated by preparative silica gel thin layer chromatography (developing solvent: ethyl acetate). Thus 47 mg of the titled compound was obtained (yield: 5%). Some portion of this product was then crystallized from ethyl acetate to thereby give pale yellow crystals.

Analytical data m.p.: 180°-182° C.

Optical purity: 100% e.e. (refer to Table 2)

Referential Example 3

Synthesis of (+)-7,8-dihydro-6,6-dimethyl-7-hydroxy-8-propionylamino-6H-pyrano[2,3-f]benz-2,1,3-oxadiazole (corresponding to compound [III*])

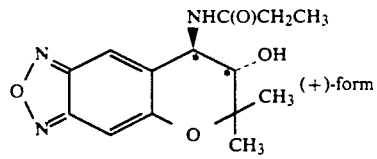

1.29 g (5.48 mmol) of (+)-7,8-dihydro-6,6-dimethyl-7-hydroxy-8-amino-6H-pyrano[2,3-f]benz-2,1,3-oxadiazole [compound (+)I], 690 mg (6.8 mmol) of triethylamine and 40 ml of methylene chloride were stirred at room temperature while 610 mg (6.6 mmol) of propionyl chloride was added thereto. The mixture was stirred at room temperature for four hours. The reaction mixture was extracted with 600 ml of ethyl acetate and 300 ml of water. The organic phase was collected and dried over anhydrous sodium sulfate. The filtrate and the residue obtained after distilling off the solvent were crystallized from a solvent mixture comprising 10 g of ethyl acetate and 5 g of hexane, allowed to stand in a refrigerator overnight and then filtered by means of suction. The obtained crystals were washed with 3-ml portions of ethyl acetate/hexane (2 1) twice and dried under reduced pressure to thereby give the titled compound in the form of a colorless product.

Analytical data m.p.: 179°-180° C.

Optical purity: 100% e.e. (refer to Table 2)

Referential Example 4

Synthesis of (-)-7,8-dihydro-6,6-dimethyl-7-hydroxy-8-propionylamino-6H-pyrano[2,3-f]benz-2,1,3-oxadiazole (corresponding to compound [III**])

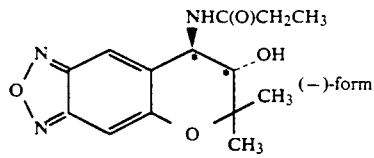

52 mg (0.22 mmol) of (-)-7,8-dihydro-6,6-dimethyl-7-hydroxy-8-(n-(1-oxo-5-chloro)pentyl)amino-6H-pyrano[2,3-f]benz-2,1,3-oxadiazole [compound (−)I], 34 μl (0.24 mmol) of triethylamine and 5 ml of methylene chloride were stirred at room temperature while 21 μl (0.24 mmol) of propionyl chloride was added thereto. The mixture was stirred at room temperature for six hours.

After the completion of the reaction, the reaction mixture was washed with water thrice and dried over anhydrous magnesium sulfate. After distilling off the solvent, the residue was recrystallized from ethanol to thereby give 15 mg of a pure titled compound (yield: 23%).

Analytical data m.p.: 179°-180° C.

Optical purity: 100% e.e. (refer to Table 2)

Referential Example 5

Synthesis of (+)-7,8-dihydro-6,6-dimethyl-7-hydroxy-8-methylureido-6H-pyrano[2,3-f]benz-2,1,3-oxadiazole (corresponding to compound (+)IV)

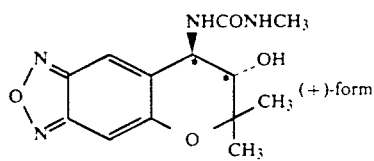

300 mg (1.28 mmol) of (−)-7,8-dihydro-6,6-dimethyl-7-hydroxy-8-amino-6H-pyrano[2,3-f]benz-2,1,3-oxadiazole [compound (+)I] and 15 ml of dichloromethane were stirred at room temperature. To the obtained solution was added 120 mg (2.10 mmol) of methyl isocyanate. The mixture was stirred at room temperature (20° C.) for five hours.

The reaction mixture was crystallized in a refrigerator and the crystals thus precipitated were filtered. Thus 214 mg of the titled compound was obtained in the form of colorless crystals (yield: 58%).

Analytical data m.p. 165°–167° C.

Optical purity: 100% e.e. (refer to Table 2)

Referential Example 6

Synthesis of (−)-7,8-dihydro-6,6-dimethyl-7-hydroxy-8-methylureido-6H-pyrano[2,3-f]benz-2,1,3-oxadiazole (corresponding to compound (−)IV)

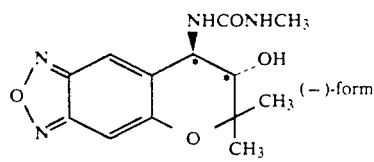

300 mg (1.28 mmol) of (−)-7,8-dihydro-6,6-dimethyl-7-hydroxy-8-amino-6H-pyrano[2,3-f]benz-2,1,3-oxadiazole [compound (−)I] and 20 ml of dichloromethane were stirred at room temperature. To the obtained solution was added 120 mg (2.10 mmol) of methyl isocyanate. The mixture was stirred at room temperature (20° C.) for five hours.

The reaction mixture was crystallized in a refrigerator and the crystals thus precipitated were filtered. Thus 195 mg of the titled compound was obtained in the form of colorless crystals (yield: 52%).

Analytical data m.p.: 165°–167° C.

Optical purity: 100% e.e. (refer to Table 2)

Referential Example 7

Synthesis of 7,8-dihydro-6,6-dimethyl-7,8-epoxy-6H-pyrano[2,3-f]benz-2,1,3-oxadiazole 3-oxide (compound [G])

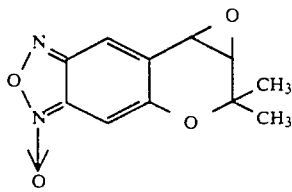

4.41 g (18.9 mmol) of 6-amino-3,4-dihydro-2,2-dimethyl-3,4-epoxy-7-nitro-2H-benzo-[b]-pyran (compound F), 1.29 g (32 mmol) of sodium hydroxide, 400 ml of ethanol and 40 ml of water were stirred at room temperature while 32.2 g (26 mmol) of a 6% aqueous solution of sodium hypochlorite was slowly added thereto dropwise. Then the obtained mixture was stirred for one hour.

After the completion of the reaction, 1 l of an aqueous solution of common salt was added thereto and the mixture was extracted with ethyl acetate thrice. The ethyl acetate phases were combined, washed with brine and dried over anhydrous sodium sulfate.

After distilling off the solvent, the residue was treated by silica gel column chromatography [developing solvent: ethyl acetate/hexane 1 : 2 (v/v)]. Thus 4.00 g of the titled compound was obtained in the form of yellow crystals (yield: 92%).

Analytical data m.p.: 144°–145° C.

Referential Example 8

Synthesis of 7,8-dihydro-6,6-dimethyl-7,8-epoxy-6H-pyrano[2,3-f]benz-2,1,3-oxadiazole (compound [H])

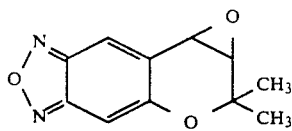

1.00 (4 27 mmol) of 7,8 dihydro-6,6-dimethyl-7,8-epoxy-6H-pyrano[2,3-f]benz-2,1,3-oxadiazole-3-oxide (compound [G]) and 6 ml of benzene were stirred at 60° C., while 0.80 ml (4.70 mmol) of triethyl phosphite was added thereto dropwise within 15 minutes. Next, the obtained mixture was stirred for three hours.

After distilled off the solvent, the residue was treated by silica gel column chromatography [developing solvent: ethyl acetate/hexane 1 : 1 (v/v)]. Thus 0.82 g of the titled compound was obtained (yield: 88%).

Some portion of this product was recrystallized from hexane to thereby give yellow crystals.

Analytical data m.p.: 97°–99° C.

Referential Example 9

Synthesis of
7,8-dihydro-6,6-dimethyl-7-hydroxy-8-amino-6H-pyrano[2,3-f]benz-2,1,3-oxadiazole (compound [(±)I])

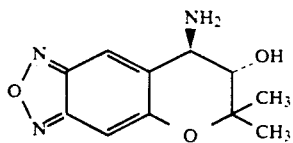

0.82 g (3.8 mmol) of 7,8-dihydro-6,6-dimethyl-7,8-epoxy-6H-pyrano[2,3-f]benz-2,1,3-oxadiazole (compound [H]) was dissolved in 25 ml of 16.7% ammonia/ethanol and then allowed to react in a pressure glass tube at 60° C. for 48 hours.

The reaction solvent was distilled off and the residue was treated by silica gel column chromatography [developing solvent: ethyl acetate/methanol 5 : 1 (v/v)] to thereby give 0.77 g of the titled compound (yield: 87%) as a brown solid.

Some portion of this product was recrystallized from ethanol to thereby give a pure titled compound in the form of colorless crystals.

Analytical data m.p.: 159°–162° C.

NMR (CDCl$_3$ +DMSO-d$_6$) δ (ppm): 1.26 (3H), 1.49 (3H), 2.80–3.30 (3H), 3.33 (1H), 3.78 (1H), 6.82 (1H) and 7.98 (1H)

Mass spectrum: 133 (50%), 163 (100%) and 235 (M$^+$, 3%)

What is claimed is:

1. An optically active pyranobenzoxadiazole compound represented by the formula [(+)I]:

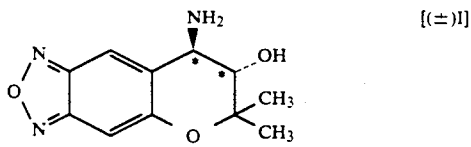

showing dextrorotation in ethanol.

* * * * *